United States Patent
Etoh et al.

[11] Patent Number: 5,867,262
[45] Date of Patent: Feb. 2, 1999

[54] SAMPLE INTRODUCING DEVICE FOR INDUCTIVELY COUPLED PLASMA ANALYZER

[75] Inventors: Toru Etoh; Yoshitomo Nakagawa, both of Chiba, Japan

[73] Assignee: Seiko Instruments Inc., Japan

[21] Appl. No.: 513,541

[22] Filed: Aug. 10, 1995

[30] Foreign Application Priority Data

Aug. 11, 1994 [JP] Japan .................................. 6-189640

[51] Int. Cl.$^6$ .......................... H01J 49/36; G01M 1/10
[52] U.S. Cl. ........................................ 356/246; 250/288
[58] Field of Search .............................. 356/246; 436/63, 436/87, 111, 112, 161, 172, 175, 177, 178, 179; 73/863, 863.01, 864.13, 864.14, 864.85; 422/64, 65

[56] References Cited

U.S. PATENT DOCUMENTS

| | | | |
|---|---|---|---|
| 4,737,342 | 4/1988 | Herrmann et al. ...................... | 422/64 |
| 4,872,353 | 10/1989 | Orr, Jr. et al. ........................ | 73/864.85 |
| 4,926,021 | 5/1990 | Streusand et al. ................. | 219/121.59 |
| 5,308,774 | 5/1994 | Miura et al. ................................ | 436/87 |
| 5,308,977 | 5/1994 | Oishi et al. ............................... | 250/288 |
| 5,381,008 | 1/1995 | Tanner et al. ............................ | 250/288 |
| 5,480,809 | 1/1996 | Salin et al. ................................ | 436/173 |

*Primary Examiner*—Frank G. Font
*Assistant Examiner*—Michael P. Stafira
*Attorney, Agent, or Firm*—Adams & Wilks

[57] ABSTRACT

A device for introducing a sample into an analyzer comprises a sample container for storing a sample solution, a fluid delivery line for delivering a volume of the sample solution from the sample container to the analyzer, and a washing fluid container for storing a washing fluid for delivery to the analyzer by the fluid delivery line to wash the fluid delivery line. A moving mechanism moves the fluid delivery line between the sample container and the washing fluid container in response to a control signal from a control apparatus to sequentially insert the fluid delivery line into the sample container and the washing fluid container for delivery of the sample solution and the washing fluid to the analyzer.

16 Claims, 4 Drawing Sheets

13 : HIGH-FREQUENCY POWER SOURCE
14 : ANALYSING DEVICE
21 : CONTROLLER
22 : TIMER
23 : DRIVING APPARATUS

13 : HIGH-FREQUENCY POWER SOURCE
14 : ANALYSING DEVICE
21 : CONTROLLER
22 : TIMER
23 : DRIVING APPARATUS

SAMPLE INTRODUCING DEVICE FOR INDUCTIVELY COUPLED PLASMA ANALYZER

BACKGROUND OF THE INVENTION

The present invention relates to a sample introducing device for introducing a sample solution into an inductively coupled plasma emission spectroscopic analyzer (hereinafter referred to as ICP-AES) or an inductively coupled plasma mass spectrometric analyzer (hereinafter referred to as ICP-MS), which performs identification and qualification of trace impurity in a sample solution.

The prior art is explained by referring to FIG. 2.

In FIG. 2, reference numeral 1 is a washing liquid, reference numeral 2 is a sample solution, reference numerals 3a and 3b are liquid feed pumps, reference numerals 4a, 4b and 4c are tubes, reference numeral 5 is a hexagonal valve, reference numeral 6 is a rotor, reference numerals 7a, 7b, 7c, 7d, 7e and 7f are joints, reference numeral 8 is a sample loop, and reference numeral 9 is a nebulizer.

The washing liquid 1 reaches the joint 7a of the hexagonal valve 5 through the liquid feed pump 3a and the tube 4a. Further, the sample solution 2 reaches the joint 7b of the hexagonal valve 5 through the liquid feed pump 3b and the tube 4b. The liquid feed pumps 3a and 3b used are a "stroke" type pump such as a peristaltic pump. When the washing liquid 1 is introduced into the nebulizer 9, the washing liquid 1 reaches the joint 7f through the hexagonal valve 5 and holes opened on the rotor 6 from the joint 7a and then reaches the nebulizer 9 through the tube 4c as shown in FIG. 2. At this time, the sample solution 2 flows in the order of the joint 7b, the sample loop 8, the joint 7e and the joint 7d from the joint 7c, and the sample loop 8 is filled with the sample solution 2. Analysis of the sample solution 2 is conducted by introducing the sample solution filled in the sample loop 8 into the inductively coupled plasma analyzer. At this time, the rotor 6 rotates, and the joints 7a and 7b, the joint 7c and 7d, and the joints 7e and 7f are connected in the hexagonal valve 5 as shown in FIG. 3.

The sample solution in the sample loop 8 is press-flown by the liquid feed pump 3a to reach the nebulizer 9.

The inductively coupled plasma analyzer is comprised of the nebulizer 9, a spray chamber 10, a plasma torch 11, a work coil 12, a high-frequency electric source, and an analyzing pipe 14. The nebulizer 9 acts to atomize the sample solution 2 or the washing liquid 1 introduced into a mist form The spray chamber 10 acts to sieve a particle diameter of the mist atomized. However, in recent inductively coupled plasma analyzers, there is an analyzer that omits the spray chamber 10 and directly leads the mist generated by the nebulizer 9 to the plasma torch The work coil 12 is wound around the tip of the plasma torch 11, and a high-frequency electric power of 27 MHz or 40 MHz is applied to the work coil 12 from the high-frequency electric source 13. By this high-frequency electric power, the mist of the sample solution 2 introduced into the plasma torch 11 forms a plasma 15 together with a gas (not shown) such as argon simultaneously introduced. The analyzing pipe 14 is a pipe to analyze an ion or a light of an impurity element contained in the sample solution in the plasma 15. The analyzing pipe 14 conducts identification of an impurity from a wavelength of light and conducts quantification from an intensity in ICP-AES, and conducts identification of impurity from a mass of an ion and conducts quantification from an intensity (ion counting rate or counting number).

However, the prior art involves the following problems. The first is a memory effect. In the conventional sample introducing device, the sample solution passes through plural joints or boundary of the rotor in the hexagonal valve, and a liquid is liable to retained at the boundary of the joints or the rotor. For this reason, when plural sample solutions are analyzed, the sample solution retained and left has influence on the analytical results of the subsequent samples. This problem is particularly important in an apparatus that conducts a super-high sensitivity analysis in ppt level, such as ICP-MS. The second is a problem on the change of an amount of the sample solution introduced into the inductively coupled plasma analyzer.

In the conventional sample introducing device the change in the amount of the sample solution introduced is required to replace the sample loop. This work is not only complicated, but also has the risk that the sample introducing device is contaminated with the external environment or the operator himself.

The present invention solves the above-mentioned problems and provides a sample introducing device which does not suffer from the disadvantages of the memory effect and contamination, and which is capable of easily changing the amount of the sample solution introduced into the inductively coupled plasma analyzer. The present invention also provides a sample introducing device for an inductively coupled plasma analyzer, which is capable of securely detecting the signal of trace impurity in the sample solution.

SUMMARY OF THE INVENTION

The present invention relates a device for introducing a sample solution into an inductively coupled plasma analyzer that performs analysis of a trace impurity in the sample solution, the device comprising a sample vessel for introducing the sample solution, a nozzle that is dipped in the sample solution to inhale the sample solution and lead the same to the inductively coupled plasma analyzer, a washing liquid tank having introduced therein a washing liquid for washing the inside of the nozzle to the inductively coupled plasma analyzer by inhaling the washing liquid from the nozzle while the sample solution is not introduced into the inductively coupled plasma analyzer, an arm for supporting the nozzle, a driving apparatus for moving the nozzle between the sample vessel and the washing liquid tank by moving the arm, and a timer that controls time for moving the driving apparatus, wherein the amount of the sample solution introduced into the inductively coupled plasma analyzer is controlled by the time that the driving apparatus operates in order to dip the nozzle in the sample solution. The present invention also relates the sample introducing apparatus for an inductively coupled plasma analyzer, characterized in that the inductively coupled plasma analyzer performs the measurement using a signal obtained after a definite time as a signal of the sample solution on the basis of a timing that the arm moves for dipping the nozzle in the sample solution.

According to the present invention, since the sample solution does not exist in areas, such as joints of the hexagonal valve or the boundary of the rotor, there is no memory effect that adversely affects the analysis. Further, since the amount of the sample solution introduced is controlled by the amount of time the nozzle is dipped in the sample solution, it can readily be changed without the tube, the joint, or the like through which the sample solution passes being touched by the operator, and the sample introducing device is not contaminated with the external environment or the operator himself.

Further, by the manner that the inductively coupled plasma analyzer performs the measurement using a signal obtained after a definite time as a signal of the sample solution on the basis of a timing that the arm moves for dipping the nozzle in the sample solution, the trace impurity to be measured can securely be detected.

EMBODIMENT

The embodiment of the present invention is explained hereinafter using FIG. 1.

Figure 1:
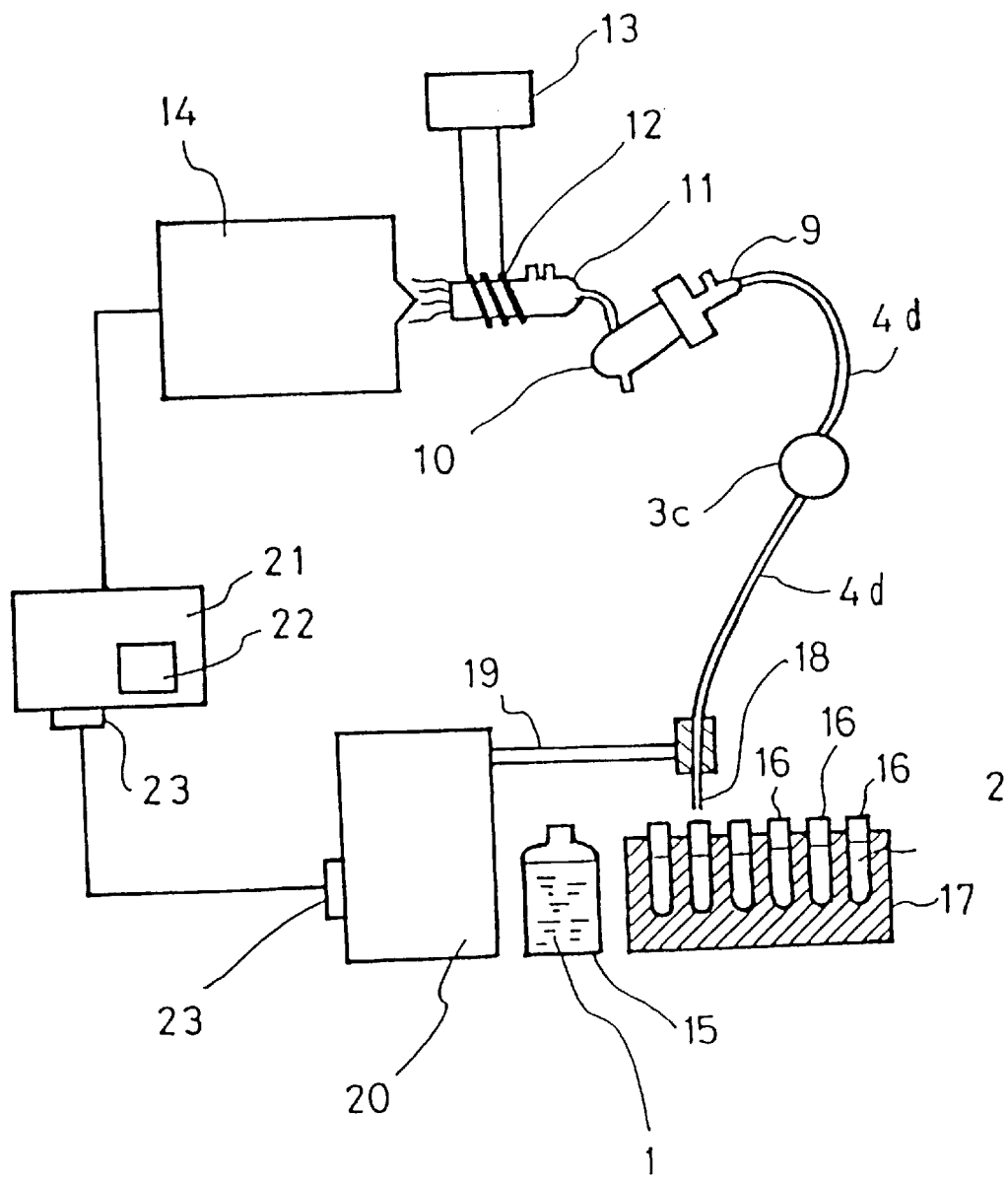
FIG. 1 is a view of a sample introducing device for an inductively coupled plasma analyzer according to the present invention.
Figure 2:
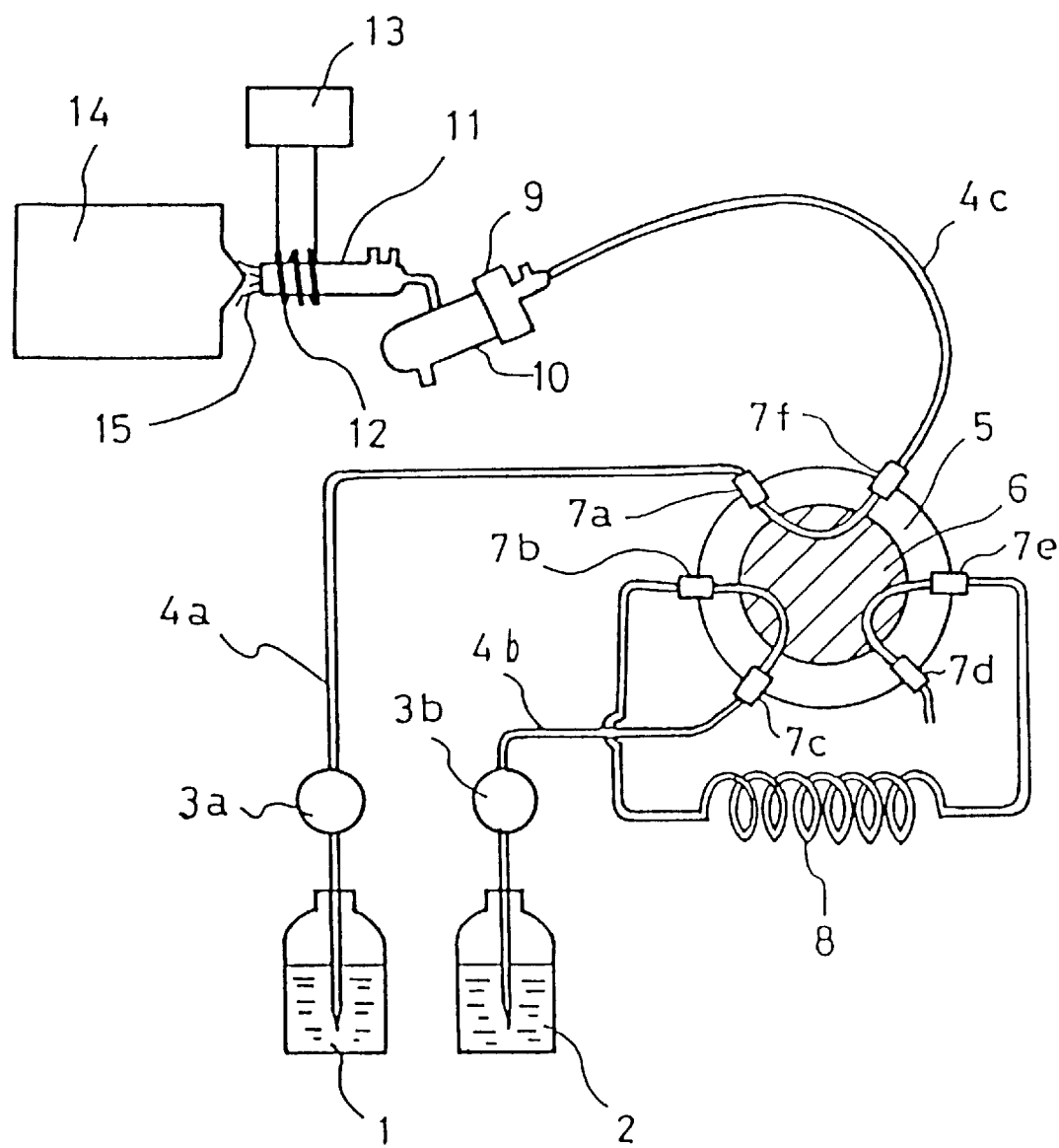
FIG. 2 is a view explaining the prior art.
Figure 3:
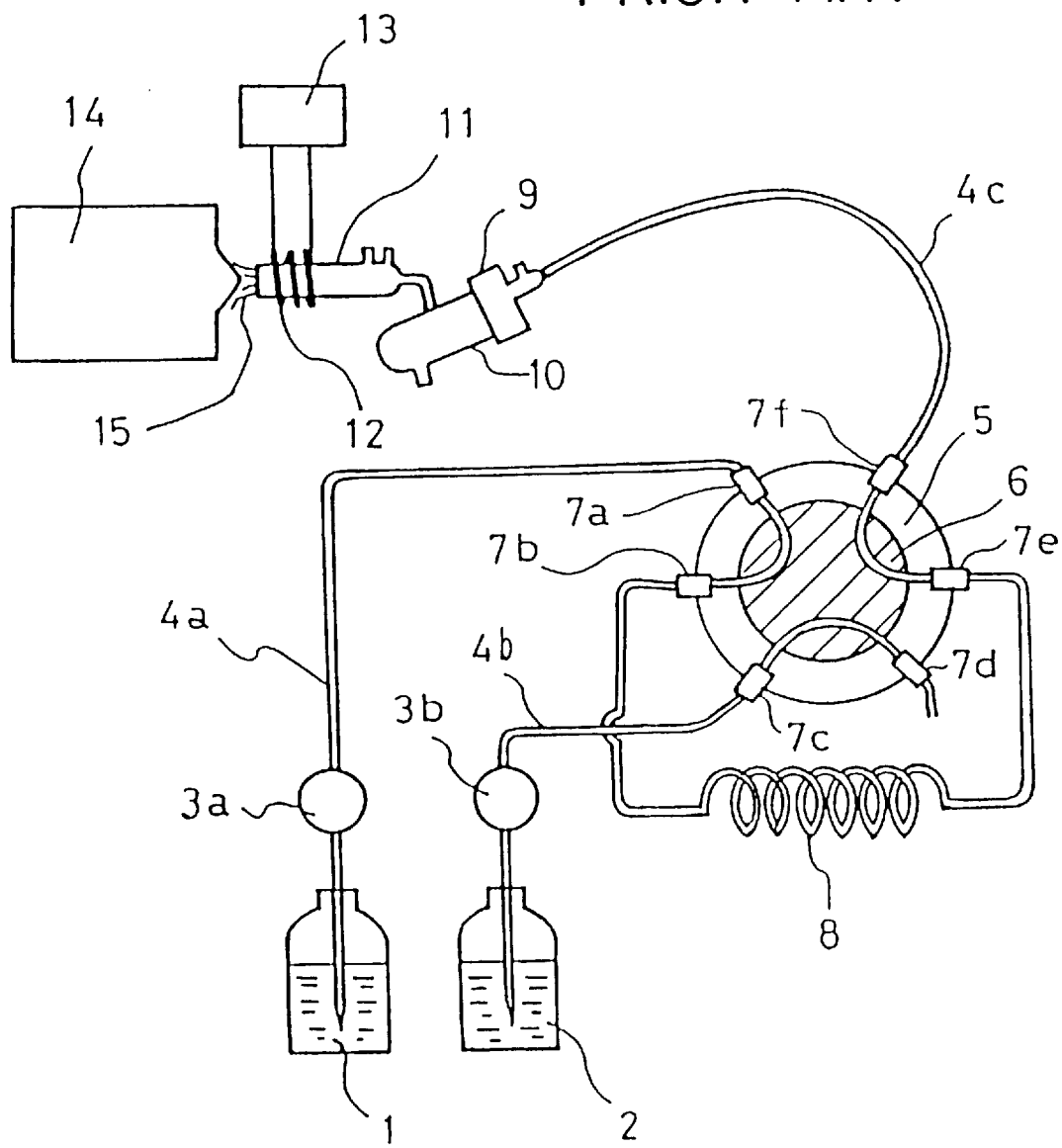
FIG. 3 is a view explaining the prior art.

In FIG. 1, the inductively coupled analyzer is comprised of the nebulizer 9, the spray chamber 10, the plasma torch 11, the work coil 12, the high-frequency electric source 13, and the analyzing pipe 14. As mentioned in the prior art, the spray chamber 10 may be omitted. Reference numeral 15 is a washing liquid tank, and a washing liquid 1 is placed therein. Reference numeral 16 is a sample vessel, and the sample solution 2 is placed therein. Reference numeral 17 is a sample table, and the sample container or vessel 16 is mounted therein. As shown in FIG. 1, it is possible for the sample table 17 to amount a plurality of the sample vessels 16.

Reference numeral 4d is a fluid delivery line or tube for delivering the washing liquid 1 or the sample solution 2 to the nebulizer 9. The tube 4d has an inner diameter of from approx 0.5 to 1.5 mm, and the material thereof used is a fluorine-type resin such as PTFE. Reference numeral 3c is the liquid feed pump, and acts to pump the washing liquid 1 or the sample solution 2 to the nebulizer 9. However, since a certain nebulizer 9 is one that can pump or inhale a solution by itself such as a concentric nebulizer, the liquid feed pump 3c may be omitted in such a case. Reference numeral 18 is a nozzle. The nozzle 18 has a structure having a hole for inhaling the washing liquid 1 or the sample solution 2, and may be a nozzle that is prepared by merely cutting the tip of the tube 4d or a tubular nozzle that is provided separately from the tube 4d. Reference numeral 19 is an arm fixed at an end thereof to the nozzle 18.

Reference numeral 20 is a driving apparatus. The driving apparatus 20 acts to horizontally move the nozzle 18 at the upper portion of the washing liquid tank 15 and the sample solution vessel 16 and also to vertically move the nozzle 18 so as to dip the nozzle 18 in the washing liquid 1 or the sample solution 2.

Reference numeral 21 is a control apparatus, reference numeral 22 is a timer, and reference numeral 23 is a communication apparatus. The control apparatus 21 can communicate with the driving apparatus 20 via the communication apparatus 23. The control apparatus 21 sends a control signal for moving the arm 19 to the driving apparatus 20 by the communication apparatus 23, and receives a signal that the movement action of the arm 19 has been completed from the driving apparatus 20. The timer 22 controls the time of the control signal. The control apparatus 21 and the timer 22 may be integrated in a body as a computer. Further, a computer that controls the inductively coupled plasma mass spectrometric analyzer may also have both functions of the control apparatus 21 and the timer 22.

The sample solution 2 is fed to the inductively coupled plasma analyzer when the nozzle 18 is lowered at the position of the sample vessel 16 to be dipped in the sample solution 2. Therefore, the amount of the sample solution 2 fed into the inductively coupled plasma analyzer is freely determined by controlling the time while the nozzle is lowered at the position of the sample vessel 16, with the control apparatus 21 and/or the timer 22. For example, when it is desired to introduce 0.1 ml of sample solution into the inductively coupled plasma mass spectrometric analyzer with the liquid feed pump 3c having a liquid feed rate of 2 ml/min., the time that the nozzle 18 is dipped or lowered into the sample solution vessel 16 is determined to be 0.05 min.

Next, a sample analysis conducted with the inductively coupled plasma mass spectrometric analyzer using the sample introducing device of the present invention is explained.

At first, the nozzle 18 is generally lowered at the position of the washing tank 15 and the washing liquid is sent to the inductively coupled plasma analyzer. When analysis is initiated, the nozzle 18 goes up from the inside of the washing tank 15, and horizontally moves to the upper portion of the next designated sample vessel 16. The nozzle 18 is then lowered to dip the same in the sample solution 2, raised after the time corresponding to the amount of the sample solution introduced, moved horizontally, and then is lowered at the position of the washing tank 15. The driving apparatus 20 sends to the control apparatus 21 "a signal that a horizontal movement of the nozzle 18 to the upper portion of the sample vessel 16 has been completed" or "a signal that a downward action of the nozzle 18 to the sample vessel 16 has been completed." On the basis of the timing to receive this "completion signal", the inductively coupled plasma analyzer performs measurement using a signal detected after a "waiting time" in a definite time as a signal of the desired trace impurity. This "waiting time" in a definite time as a signal of the desired impurity element corresponds to the time until the sample solution 2 is moved through the tube 4d and is detected in the analyzing pipe 14 as a signal, and mainly depends on the volume of the tube 4d and the liquid feed rate of the liquid feed pump 3c.

Figure 4:
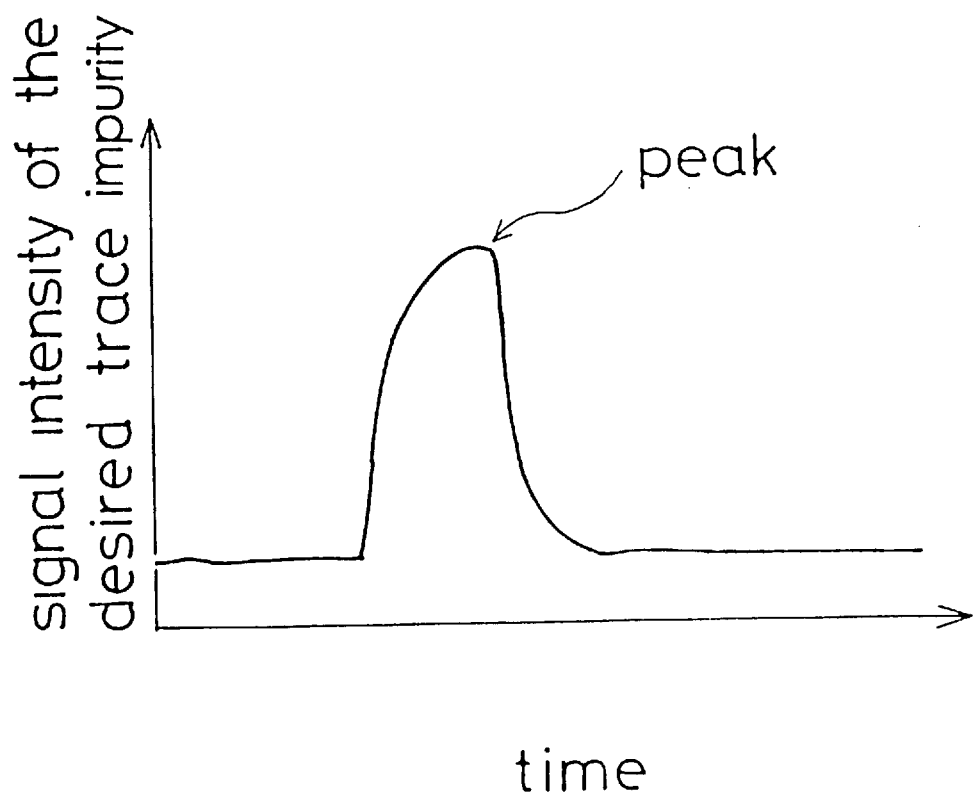
FIG. 4 is a graph showing a change with the passage of time of a signal of the desired trace impurity.

FIG. 4 is a graph showing a change with the passage of the time of a signal intensity of the desired trace impurity. A peak shown in FIG. 4 corresponds to a signal of the trace impurity contained in the sample solution 2. A time of from the "completion signal" to a rise of this peak corresponds to the "waiting time." In the inductively coupled plasma analyzer, the concentration of the desired trace impurity is calculated from a height or an area of the peak showing in FIG. 4. By determining the "waiting time," the peak of the desired trace impurity can securely be abtained, and analysis having a high reliability can be conducted. When the detection of the desired trace impurity is completed, the nozzle 18 of the sample introducing device moves to the next sample vessel 16, and the above procedures are repeated to continue the analysis.

According to the present invention, there is no memory effect that adversely affects the analysis. Further, the amount of the sample solution introduced can readily be changed without the tubes, the joints, or the like through which the sample solution passes being touched by the operator, and also the sample introducing device is not contaminated with the external environment or the operator himself.

Further, the trace impurity to be surely measured can be securely detected. Thus, the present invention enables a highly reliable analysis to be conducted.

What is claimed is:

1. A device for introducing a sample solution into an inductively coupled plasma analyzer that performs analysis of a trace impurity in the sample solution, the device comprising: a sample vessel for storing a sample solution; a fluid delivery tube having a nozzle for dipping into the sample solution in the same vessel to withdraw the sample solution and deliver the sample solution to an inductively coupled plasma analyzer; a washing liquid tank for storing a washing liquid for delivery to the inductively coupled plasma analyzer by the fluid delivery tube to wash the inside of the fluid delivery tube at a time when the sample solution is not being introduced into the inductively coupled plasma analyzer; an arm for supporting the fluid delivery tube at the nozzle; a driving apparatus connected to the arm and responsive to a control signal from a control apparatus for moving the nozzle between the sample vessel and the washing liquid tank by movement of the arm to sequentially dip the nozzle of the fluid delivery tube into the sample vessel and the washing liquid tank; and a timer for controlling a time of the control signal from the control apparatus; wherein the amount of the sample solution introduced into the inductively coupled plasma analyzer is controlled by the time that the control signal controls the driving apparatus to dip the nozzle of the fluid delivery tube into the sample solution.

2. The sample introducing device for an inductively coupled plasma analyzer as claimed in claim 1, characterized in that the inductively coupled plasma analyzer performs the measurement using a signal obtained after a definite time as a signal of the sample solution on the basis of a timing that the arm moves for dipping the nozzle in the sample solution.

3. A device as set forth in claim 1; further comprising withdrawing means for withdrawing through the fluid delivery tube the sample solution from the sample vessel or the washing liquid from the washing liquid tank when the fluid delivery tube is dipped into the sample vessel or the washing liquid tank, respectively.

4. A device as set forth in claim 3; wherein the withdrawing means comprises a peristaltic pump.

5. A device as set forth in claim 3; wherein the peristaltic pump is connected to the fluid delivery tube independently from the inductively coupled plasma analyzer.

6. A device as set forth in claim 3; wherein the withdrawing means is incorporated in a concentric nebulizer of the inductively coupled plasma analyzer.

7. An inductively coupled plasma analyzer having a device for introducing a sample solution as set forth in claim 1.

8. A device for introducing a sample solution into an analyzer, comprising:

a sample container for storing a sample solution;

a fluid delivery line for delivering a volume of the sample solution from the sample container to the analyzer;

a washing fluid container for storing a washing fluid for delivery to the analyzer by the fluid delivery line to wash the fluid delivery line;

moving means for moving the fluid delivery line between the sample container and the washing fluid container and for sequentially inserting the fluid delivery line into the sample container and the washing fluid container only for delivery of the sample solution and the washing fluid to the analyzer;

withdrawing means for withdrawing through the fluid delivery line the sample solution from the sample container or the washing fluid from the washing fluid container when the fluid delivery line is inserted in the sample container or the washing fluid container, respectively, for delivery of the sample solution or the washing fluid to the analyzer; and control means for controlling the moving means to effect insertion of the fluid delivery line into the sample container or into the washing fluid container to effect withdrawal of the sample solution or the washing fluid, respectively, through the fluid delivery line for delivery to the analyzer.

9. A device as set forth in claim 8; wherein the withdrawing means comprises a peristaltic pump.

10. A device according to claim 9; wherein the peristaltic pump is connected to the fluid delivery line independently from the analyzer.

11. An inductively coupled plasma analyzer having a device for introducing a sample solution as set forth in claim 8.

12. An inductively coupled plasma analyzer as set forth in claim 11; further comprising a nebulizer, the withdrawing means being incorporated in the nebulizer.

13. An inductively coupled plasma analyzer having a device for introducing a sample solution as set forth in claim 2.

14. A device for introducing a sample solution into an analyzer, comprising:

a sample container for storing a sample solution;

a fluid delivery line for delivering a volume of the sample solution from the sample container to the analyzer;

a washing fluid container for storing a washing fluid for delivery to the analyzer by the fluid delivery line to wash the fluid delivery line;

a control apparatus for producing control signals for controlling movement of the fluid delivery line;

a timer for controlling a time of the control signals from the control apparatus;

a driving apparatus responsive to the control signals for selectively positioning the fluid delivery line over the sample container and the washing fluid container and for sequentially inserting the fluid delivery line into the sample container and the washing fluid container only for delivery of the sample solution and the washing fluid to the analyzer; and withdrawing means for withdrawing through the fluid delivery line the sample solution from the sample container or the washing fluid from the washing fluid container when the fluid delivery line is inserted in the sample container or the washing fluid container, respectively, for delivery of the sample solution or the washing fluid to the analyzer;

wherein the amount of the sample solution introduced into the analyzer is controlled by the time that a control signal from the control apparatus controls the driving apparatus to insert the fluid delivery line into the sample solution.

15. A device as set forth in claim 14; wherein the withdrawing means comprises a peristaltic pump.

16. A device as set forth in claim 15; wherein the peristaltic pump is connected to the fluid delivery line independently from the analyzer.

* * * * *